United States Patent [19]

Mehl

[11] Patent Number: 5,049,148
[45] Date of Patent: Sep. 17, 1991

[54] RADIO FREQUENCY HAIR REMOVAL TWEEZER

[76] Inventor: Thomas L. Mehl, P.O. Box 1019, Newberry, Fla. 32669

[21] Appl. No.: 372,852

[22] Filed: Jun. 29, 1989

[51] Int. Cl.$^5$ ............................................. A61B 17/41
[52] U.S. Cl. ....................................... 606/43; 606/51; 606/52
[58] Field of Search .................. 606/43, 36, 51, 52

[56] References Cited

U.S. PATENT DOCUMENTS

| | | | |
|---|---|---|---|
| 4,074,718 | 2/1978 | Morrison, Jr. | 606/51 X |
| 4,174,713 | 11/1979 | Mehl | 606/43 X |
| 4,311,145 | 1/1982 | Esty et al. | 606/51 X |

FOREIGN PATENT DOCUMENTS

| | | | |
|---|---|---|---|
| 3447156 | 7/1986 | Fed. Rep. of Germany | 606/51 |
| 83/02389 | 7/1983 | World Int. Prop. O. | 606/43 |

*Primary Examiner*—Lee S. Cohen

[57] ABSTRACT

A radio frequency hair removal tweezer assembly having an accurately formed lead-conductor pad configuration for providing greater radio frequency transmission capability. A raised conductor surface and angular inclination of the pad members permits forceful grasping of the hair and improved radio frequency transmission down the hair shaft. An integrally molded unitary tweezer unit is positioned within a split two piece housing assembly and results in rapid and accurate assembly of the working components and elimination of high rejection rates of previous similar tweezer units.

12 Claims, 2 Drawing Sheets

5,049,148

RADIO FREQUENCY HAIR REMOVAL TWEEZER

BACKGROUND OF THE INVENTION

Radio frequency hair removal tweezers have been successfully used to remove unwanted hair by applying radio frequency energy through the tip of a hand-held hair grasping tweezer unit.

One of the most effective designs of this type of unit is that shown and described in the Thomas L. Mehl U.S. Pat. Nos. 4,174,713, 4,174,714 and 4,566,454. This unit permitted the user to come close to the skin with the tweezer tip without bringing about a burn as a result of RF arcing to the skin surface. It also delivered more radio frequency energy down the hair shaft, effectively inhibiting regrowth of the hair from the hair follicle.

Although the tweezer unit worked effectively, the design did not produce maximum power transfer to the hair and also brought about high rejection rates of the production model.

SUMMARY OF THE INVENTION

Consequently, this invention is directed to providing a modified and improved radio frequency hair removal tweezer unit which transmits radio frequency energy more effectively, and which can be produced at a high production rate with a low percentage of rejections.

Further, this invention uses an improved radio frequency conductor wire design which more effectively transmits radio frequency waves to the hair shaft. It also provides improved tweezer arms which substantially enhance the ability to effectively grip the hair shaft by providing an angular relative orientation between opposed tweezer RF conducting pads at the tip of the tweezer for more effectively providing a forceful contact with the hair shaft.

Additionally, the conducting pads are arranged above the adjacent plastic tweezer arm material to avoid the possibility of that material interfering with complete closure of the tweezer pads about the hair shaft.

The tweezer of this invention also provides an instrument in which radio frequency energy is always available for use with no need to provide a switch element to interrupt radio frequency supplied to the radio frequency conductor pads.

These and further features of this invention will become apparent from the drawings and the following description of the invention.

DESCRIPTION OF THE DRAWINGS

Referring particularly to the drawings.

DESCRIPTION OF THE INVENTION

Figure 1:
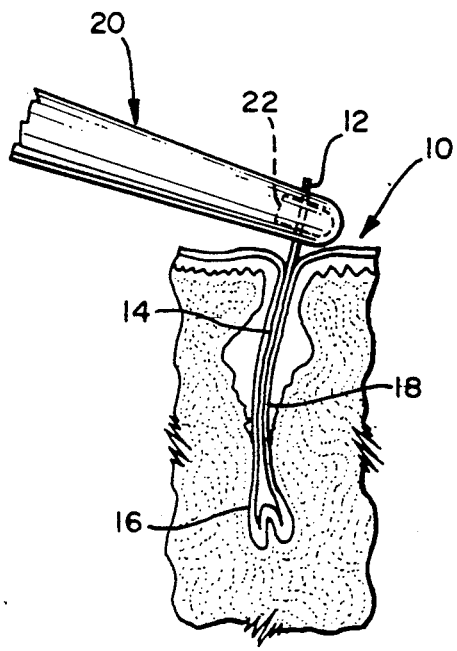
FIG. 1 is a cross-sectional view of a hair in position within a tissue and held between the free engaging ends of an RF radio frequency (RF) tweezer.
Figure 2:
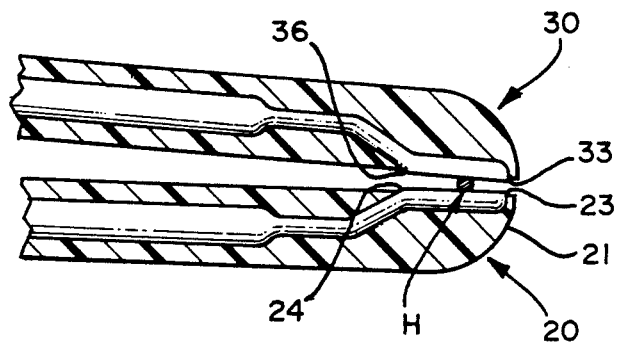
FIG. 2 is an enlarged partial view of FIG. 1 showing the manner in which the tweezer tips engage the hair shaft.
Figure 3:
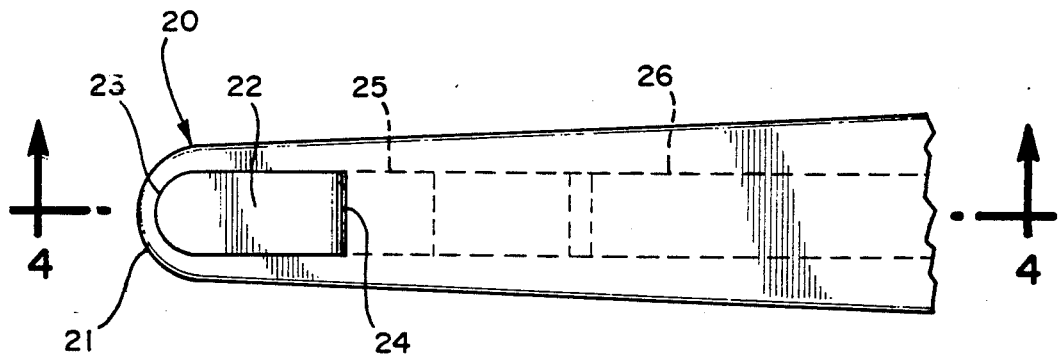
FIG. 3 is a plan view of one of the tweezer tips shown in FIG. 2.

Referring particularly to FIGS. 1 and 2, a section of tissue containing a hair generally indicated at 10 has the external portion 12 of the hair shaft extending upwardly from the skin surface, while the internal portion of 14 of the hair shaft extends downwardly beneath the skin surface to the hair follicle 16. The hair has a central core section 18 which conducts radio frequency energy along the length of the hair to the hair follicle.

The external section of the hair shaft is shown grasped between the two opposed tweezer arm ends 20 and 30.

The two opposed tweezer arms are each similar in construction and carry opposed metal RF frequency conducting pads, 22, 32, which contact and grasp between them the external hair shaft portion 12. The pads are disposed at a small angle with respect to each other and initially make contact at their forward edges 24, 34, and then close into full contact with other on flexure of the tweezer arms.

Both the tweezer arms are identical in construction.

The tweezer itself is an injection molded piece, which, as can be seen in FIGS. 5 through 8, is supported within the forward portion of a had-held cylindrical handle. The tweezer itself is an injection molded piece with a central plug section from which both tweezer arms 20 and 30 extend. The tweezer is slightly lager than an ordinary tweezer and is made of a flexible plastic such as acrylic resin, or other molded material. The tweezer arms carry a wire conductor and have some flexibility.

The tip of the tweezer 21 is rounded and is slightly over $\frac{1}{8}$ of an inch in width. The conducting pad 22 a flat conducting surface, which is preferably gold plated. It has a rounded forward periphery 23 which is slightly greater than $\frac{1}{8}$ of an inch in width, and extends about 3/16 of an inch from the forward periphery 23 to the rear edge 24. The surrounding insulation of plastic around the pad is about 1/32 of an inch wider.

The conducting pad 24 is connected to an angled flat intermediate connecting section which in turn is integral with the end of a circular solid copper lead wire 26.

The conducting pad 22 and the intermediate connector section are produced by inserting the end of a round wire copper lead into a stamping die which, on closing, flattens the wire, forming the pad and intermediate connection sections on the end of the wire. This provides an accurate and closely dimensioned piece which can also be readily and accurately positioned in an injection cavity mold.

Figure 4:
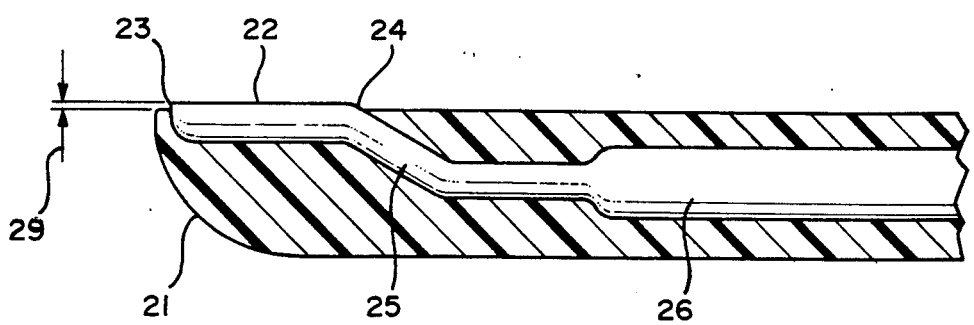
FIG. 4 is a sectional view of the tweezer tip along line 4—4 of FIG. 3.

It should be noted that the conducting pad surface, which is preferably gold plated, is also slightly raised above the surface of the plastic surface of the tweezer as shown in FIG. 4 at 29 to provide a clearance which is no less than 1/32 of an inch. Because of the clearance, the two opposed conductor pad surfaces can come together in non-interfering engagement, and as shown in FIG. 2, are sufficiently clear to permit the conducting pad forward surfaces 23 and 33 to come into initial engagement at a slight angle. Subsequent pressure on the tweezer arms 20 and 30 flexes the two elongated arms, brining the full length of the surfaces of the pads 22 and 32 into full and forceful engagement with each other. This arrangement precludes the possibility of an interference with full and complete closure that might possibly result, if the plastic material of the tweezer arm happened to be higher than the pad surface.

These figures illustrate the criticality of the dimension and the positioning of the pads and their leads within the tweezer arm, since the width of the surrounding plastic is only about 1/32 of an inch. The shape of the pad and integral lead permit it to be accurately positioned in the mold. Previously, this has not been possible. One of the difficulties encountered was that due to the thinness of the tweezer arm and the enclosing plastic surrounding the conductor and the conducting surface at the tip of the tweezer, accurate positioning of the elements was not always possible and the wire conductor and conducting surface frequently was not covered with the insulating plastic of the tweezer or molding. Such tweezer pieces had to be rejected.

With the construction of this invention, in which the end of the conductor is accurately stamped in a tight tolerance press, to produce the combined pad and lead as a single accurate integral piece which can be accurately positioned within the mold cavity, the problem encountered with the previous production item is avoided.

In addition, the approach of providing a fully single conducting pad-lead stamped piece for conducting the radio frequency, provides a good radio frequency wave guide configuration with more radio frequency carrying capability, with less loss. Little change in sectional configuration and no sharp break in RF path insures greater RF frequency transmission to the surface of the pad. The pad surface itself, which is preferably gold plated, also contributes to more effective power transmission of the radio frequency to the hair itself. The usual frequency applied to the lead 26 is 15,000 hertz at approximately 100 volts.

The entire hand-held tweezer assembly is shown in FIGS. 5 through 8. The injection molded tweezer consisting of arms 20 and 30, and the cylindrical support base 40 fit into a split two piece cylindrical handle housing formed by the two identical molded and split pieces 70 and 80. These are snapped together along adjacent longitudinally extending faces.

Figure 5:
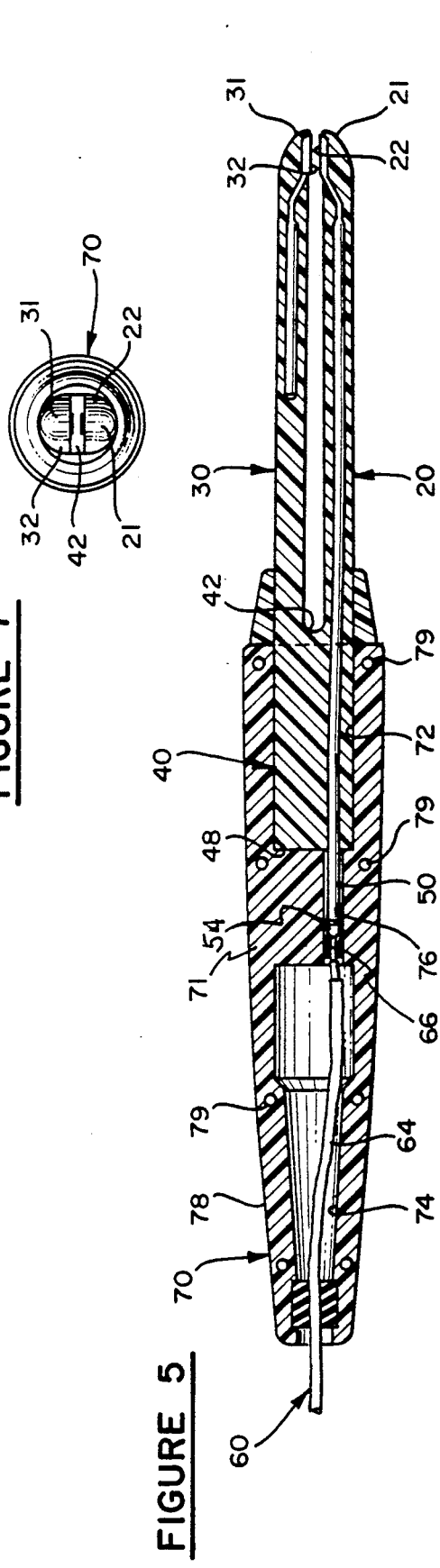
FIG. 5 is a side view of the radio frequency tweezer and holder assembly, showing the tweezer in cross-section.
Figure 6:
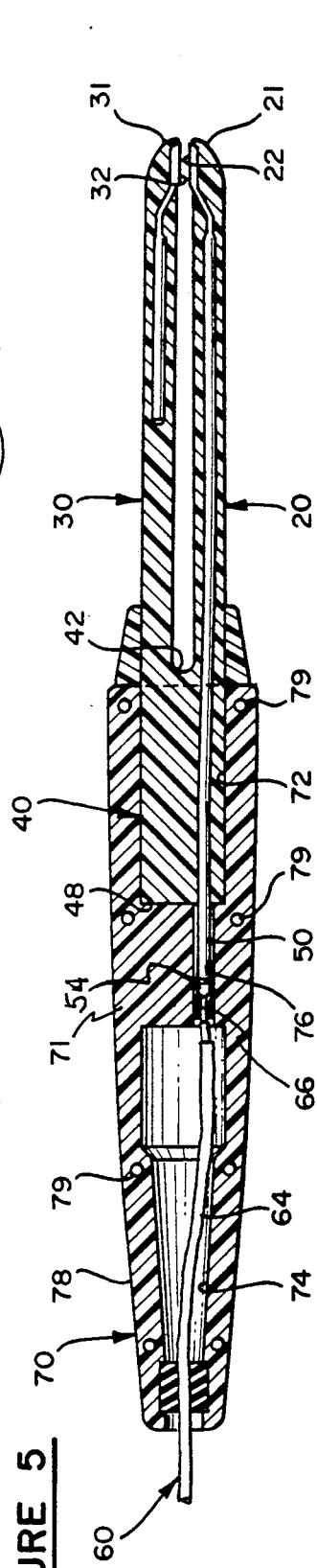
FIG. 6 is a top view of the RF tweezer and holder assembly of FIG. 5.
Figure 7:
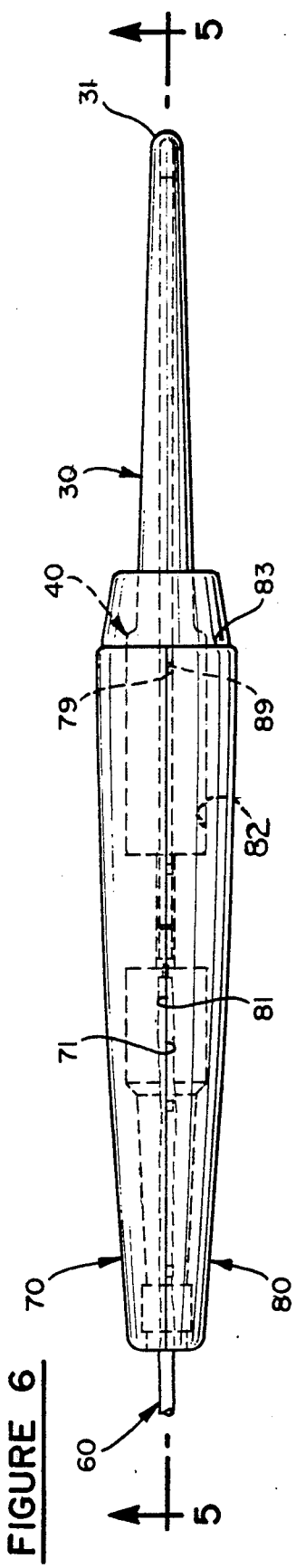
FIG. 7 is an end view of the tweezer of FIG. 6.
Figure 8:
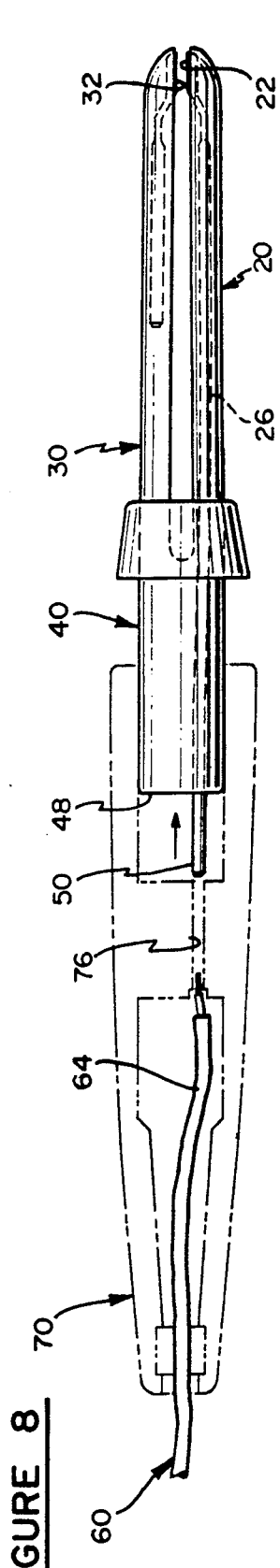
FIG. 8 is a phantom view of the tweezer of FIG. 5 showing the electrical connection to the RF tweezer.

The tweezer assembly cylindrical section 40 is received within the forward cavity defined by the semi-cylindrical sections 72 and 82, as illustrated in FIGS. 5 and 6. The positive radio frequency lead 26 of tweezer arm 20 extends outwardly beyond the rearward surface 48 of the cylindrical tweezer base 40. The tweezer arms 20 and 30 are spaced substantially from each other at the front face indicated at 42 to permit the tweezers at their ends to move into engagement at an angular inclination for firm pad engagement. The flat side face 71 of the housing piece 70 has a forward elongated semi-cylindrical receiving cavity 72 for receiving half of the tweezer section 40. A rear power line receiving cavity 74 accommodates the internal radio frequency supply line 64 of radio frequency supply cable 60. Conductor receiving sleeve 50 is disposed within the channel 76 and is interconnected with the frequency supply wire 66 at 54.

In this tweezer modification, it is not necessary to have a power supply button. The power is continuously supplied to the lead wire Z6 of the tweezer arm Z0. It should also be noted that the conductor pad 32 of tweezer arm 30 has only a small lead 36. This is completely isolated, not being connected to either a ground or radio frequency supply cable. The tweezer has been found to work effectively with this electrical arrangement. Apparently, only a contact pad opposing the pad supplying the radio frequency energy in the opposing tweezer arm, is necessary. The rear external surface of the handle is tapered as indicated at 78. The pin members 79 extend outwardly from the flat side face 71 of housing 70. They extend into openings 89, not shown, in the opposing matching surface 81 of the semi-cylindrical housing element 80.

Accordingly, the new tweezer design described provides greater hair gripping capability, and better radio frequency transmission through the conductor pad to the hair. This results in about a ⅓ or greater reduction in the amount of time, originally 10 to 20 seconds, required for removal of the hair.

The construction of this tweezer unit is simplified with three accurately molded major components which are accurately and readily assembleable. The re-design of the tweezer itself provides a production item which will overcome the 20 to 25 percent rejection rate encountered with the previously designed tweezer.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

What is claimed is:

1. A radio frequency hair removal tweezer comprising:
   a) a hand-held housing to which radio frequency energy is supplied which has a forward end supporting a pair of tweezer arms extending outwardly therefrom;
   b) the tweezer arms being a pair of relatively movable opposed and spaced flexible plastic members which are movable into contact with each other at their opposed free ends at a small angle with respect to each other;
   c) each of the tweezer arms at their opposed free ends having a flat interior surface facing each other;
   d) the facing interior surfaces having a radio frequency conducting hair engaging metal conducting pad with a flat surface whose periphery is slightly spaced from the outer periphery of the flat interior surface of the tweezer;
   e) each of the conducting pad surfaces being raised slightly above the flat interior surface of ht tweezer free ends, whereby the tweezer arms can bring the opposed pads together at their extremities at a slight angle with no interference from the adjacent plastic surface to provide a firm forceful contact between the opposed conducting pad surfaces; and
   f) at least one of the tweezer arms having a conducting pad lead wire which extends the length thereof and is connected with the conducting pad at the free end.

2. The radio frequency hair removal tweezer as set forth in claim 1, wherein:
   a) a tweezer support base is disposed at the forward end of the housing from which the tweezer arms extend;
   b) the tweezer support base and the tweezer arms being a unitary molded piece; and c) the tweezer support base having an electrical lead extending there through and being integral with the conducting pad lead wire.

3. The radio frequency hair removal tweezer as set forth in claim 2, wherein:
 a) the conducting pad lead wire has an extended section which extends rearwardly of the tweezer support base; and
 b) the housing contains an electrical connector receptacle which receives the extended section of the conducting lead wire.

4. The radio frequency hair removal device as set forth in claim 1, wherein:
 a) the flat conducting surface of at least one conducting pad has a gold plated conducting surface.

5. The radio frequency hair removal device as set forth in claim 1, wherein:
 a) the conducting pad is an integral continuous part of the conducting pad lead wire;
 b) the conducting pad being connected to the conducting pad lead wire through a flattened intermediate connection section; and
 c) the conducting pad and the intermediate flattened section, both being formed from an end portion of the conducting pad lead wire.

6. The radio frequency hair removal device as set forth in claim 1, wherein:
 a) the hand-held housing is an assembly of two matching substantially identical housing elements having corresponding engaging faces which meet along a common substantially longitudinal plane.

7. The radio frequency hair removal tweezer as set forth in claim 6, wherein:
 a) each of the housing elements has an open semi-cylindrical cavity at the forward end receiving cylindrical tweezer base element which supports the tweezer arms.

8. The radio frequency hair removal device as set forth in claim 7, wherein:
 a) one of the housing elements has plural outwardly projecting pins extending form a flat longitudinally extending engaging face; and
 b) the other housing element has a corresponding flat engaging face and plural pin receiving recesses in its corresponding flat engaging face which are disposed opposite from and receive the outwardly extending pins from the one housing element.

9. The radio frequency hair removal tweezer as set forth in claim 1, wherein:
 a) the conducting pad lead wire is directly connected continuously to a radio frequency power supply line.

10. The radio frequency hair removal tweezer as set forth in claim 1, wherein:
 a) the conducting pad lead wire and the radio frequency conducting pad are a single integral element having good radio frequency wave guide transmission characteristics.

11. A radio frequency hair removal tweezer comprising:
 a) a hand-held housing to which radio frequency energy is supplied which has a forward end supporting a pair of tweezer arms extending outwardly therefrom;
 b) the tweezer arms being a pair of relatively movable opposed and spaced flexible plastic members which are movable into contact with each other at their opposed free ends at a small angle with respect to each other;
 c) each of the tweezer arms at their opposed free ends having a flat interior surface facing each other;
 d) the facing interior surfaces having a radio frequency conducting hair engaging metal conducting pad with a flat surface whose periphery is slightly spaced from the outer periphery of the flat interior surface of the tweezer such that the two surfaces can be brought into direct contact with each other;
 e) a conducting pad lead wire of solid metal cross-section disposed in one of the tweezer arms and has as an integral continuous part thereof forming a conducting pad;
 f) the conducting pad is connected to the conducting pad lead wire through a flattened intermediate and offsetting connection section; and,
 g) the conducting pad and the intermediate flattened offsetting section are both formed from an end portion of the conducting pad lead wire.

12. The radio frequency hair removal tweezer as set forth in claim 11, wherein:
 a) the flat surface of at least one conducting pad as a gold plated conducting surface;
 b) the hand-held housing is an assembly of two matching substantially identical housing elements having longitudinally engaging faces which meet along a common substantially longitudinal plane.

* * * * *